United States Patent
Cho

(10) Patent No.: US 11,679,085 B2
(45) Date of Patent: Jun. 20, 2023

(54) PATCH FOR ALLEVIATION AND PREVENTION OF ACNE

(71) Applicant: LABNPEOPLE CO., LTD., Gyeonggi-do (KR)

(72) Inventor: Sung Youn Cho, Gyeonggi-do (KR)

(73) Assignee: LABNPEOPLE CO., LTD., Gyeonggi-Do (KR)

( * ) Notice: Subject to any disclaimer, the term of this patent is extended or adjusted under 35 U.S.C. 154(b) by 0 days.

(21) Appl. No.: 17/057,103

(22) PCT Filed: May 21, 2019

(86) PCT No.: PCT/KR2019/006068
§ 371 (c)(1),
(2) Date: Nov. 20, 2020

(87) PCT Pub. No.: WO2019/225948
PCT Pub. Date: Nov. 28, 2019

(65) Prior Publication Data
US 2021/0196649 A1    Jul. 1, 2021

(30) Foreign Application Priority Data

May 21, 2018 (KR) .................. 10-2018-0057629
May 20, 2019 (KR) .................. 10-2019-0058730

(51) Int. Cl.
A61K 33/30 (2006.01)
A61K 9/70 (2006.01)
A61P 17/10 (2006.01)
A61K 9/00 (2006.01)

(52) U.S. Cl.
CPC .......... *A61K 9/7023* (2013.01); *A61K 9/0021* (2013.01); *A61K 33/30* (2013.01); *A61P 17/10* (2018.01)

(58) Field of Classification Search
CPC .... A61K 9/7023; A61K 9/0021; A61K 33/30; A61P 17/10
See application file for complete search history.

(56) References Cited

U.S. PATENT DOCUMENTS

2014/0276362 A1* 9/2014 Alvarez ................ A61K 33/00
                                                    604/21
2016/0022876 A1* 1/2016 Imwinkelried .......... A61F 2/44
                                                    623/1.15

FOREIGN PATENT DOCUMENTS

| JP | 2000159632 A | 6/2000 |
| KR | 1020110065391 A | 6/2011 |
| KR | 1020120062243 A | 6/2012 |
| KR | 1020150100227 A | 9/2015 |
| KR | 1020150121053 A | 10/2015 |
| KR | 101622388 B1 | 5/2016 |
| KR | 1020160058261 A | 5/2016 |
| KR | 1020170115449 A | 10/2017 |
| KR | 1020180004202 A | 1/2018 |
| WO | 2006116281 A2 | 11/2006 |
| WO | WO-2009142741 A1 * | 11/2009 .......... A61B 17/205 |

OTHER PUBLICATIONS

Akiko Tyamamoto, "Biomedical Application of Biodegradable Magnesium Alloys", Journal of the Surface Finishing Society of Japan, vol. 62, No. 4, 2011, pp. 204-210, Japan, 8pp.

Emil A, Tanghetti, MD, The Role of Inflammation in the Pathology of Ache, Clinical L. Aesthetic, Sep. 2013, pp. 27-35, vol. 6, No. 9, 9pp.

* cited by examiner

*Primary Examiner* — Ali Soroush
(74) *Attorney, Agent, or Firm* — Hauptman Ham, LLP

(57) ABSTRACT

Proposed is a patch for the alleviation and prevention of acne, in which anti-acne activity of a biodegradable metal represented by $Mg_aZn_bX_c$ (in which a, b and c are wt % of individual components, a+b+c=100 wt %, 0≤a≤100, 0≤b≤100, and 0≤c≤10, among which a or b is the greatest, and X is at least one selected from the group consisting of Ca, Fe, Mn, Si, Na, Zr, Ce, and P) is demonstrated, thus exhibiting novel use thereof as a patch for the alleviation and prevention of acne.

12 Claims, 16 Drawing Sheets

FIG. 15

■ The Global Acne grading System(GAGS)

\* Local score = Location factor × Grade(0–4)\*

| | Location | Factor |
|---|---|---|
| I | Forehead | 2 |
| II | Right cheek | 2 |
| III | Left cheek | 2 |
| IV | Nose | 1 |
| V | Chin | 1 |
| VI | chest and upper back | 3 |

■ Global Score

| | |
|---|---|
| 0 | None |
| 1–18 | Mild |
| 19–30 | Moderate |
| 31–38 | Severe |
| >39 | Very Severe |

\* Grade\*: 0(No lesions), 1(≥ one comedone),
2(≥ one papule), 3(≥ one pustule), 4(≥ one nodule)

FIG. 16

■ Skin irritation evaluation (adverse reaction)

* Condition of test subject is judged and irritation and irritation site are recorded

*Adverse grading
0: none( No adverse reaction ), 1: mild, 2: severe, 3: very severe( Severe adverse reaction )

| Erythema | Edema | Scaling | Itching | Stinging | Burning | Tightness | Prickling |
|---|---|---|---|---|---|---|---|
|  |  |  |  |  |  |  |  |

PATCH FOR ALLEVIATION AND PREVENTION OF ACNE

RELATED APPLICATIONS

The present application is a national phase of International Application Number PCT/KR2019/006068, filed May 21, 2019, which claims priority to Korean Application Number 10-2018-0057629, filed May 21, 2018 and Korean Application Number 10-2019-0058730, filed May 20, 2019.

TECHNICAL FIELD

The present disclosure relates to a patch for the alleviation and prevention of acne, and more particularly to the novel use of a biodegradable metal containing magnesium as a main component.

BACKGROUND ART

Thorough research into microneedles has been carried out since 1998 when Prausnitz and associates at Georgia Tech in the United States made a microneedle array with a silicon device using semiconductor-processing technology and suggested the possibility of application thereof to drug delivery. When a microneedle is inserted into the skin, sufficiently high physical strength thereof has to be maintained so that the microneedle may be inserted without being bent or broken, and thus properties enabling shape control and strength suitable therefor are required. In order to satisfy these properties, stainless steel has been used as the material for a microneedle, but in the case in which small particles thereof are left behind in the body, there is a problem of inflammation, and in the case of polymers (PLA, PGA, biodegradable copolymer), there is a problem in that penetration does not occur.

Korean Patent Application Publication No. 2016-0058261 discloses a water-soluble microneedle made of a material such as polyglycolide (PGA), polylactide-glycolide copolymer (PLGA), hyaluronic acid, alginic acid, pectin, etc. and a method of manufacturing the same, Korean Patent No. 1622388 discloses a silicon microneedle stamp and a method of manufacturing the same, and Korean Patent Application Publication No. 2015-0121053 discloses a microneedle made of a material such as silicon, silicon dioxide, ceramics, metals (stainless steel, titanium, nickel, molybdenum, chromium, cobalt, etc.) and synthetic or natural resins and coated with a Japanese encephalitis vaccine antigen.

As described above, the microneedle developed to date is an alternative drug administration means capable of replacing a drug delivery mode through oral administration or a drug delivery mode through injection, and has been used as a device, namely a kind of drug carrier, capable of delivering a drug through the epidermis without stimulating nociceptive nerves distributed throughout the skin.

Meanwhile, Korean Patent Application Publication No. 2017-0115449 filed and laid open by the present applicant discloses a microneedle using a biodegradable metal and a patch including the same. Here, it has been confirmed that the microneedle is useful as a drug carrier and is also effective at reducing wrinkles when used alone due to the action thereof as a mineral.

DISCLOSURE

Technical Problem

An objective of the present disclosure is to provide the novel use of a biodegradable metal, which is the main component of a microneedle conventionally developed as a drug delivery means.

In particular, the present disclosure confirms that a biodegradable metal, which has been used as the main component of a microneedle, exhibits antibacterial activity when used alone against an acne pathogen, even without the need to additionally include a drug, and is intended to provide the novel use of a specific biodegradable metal for the alleviation and prevention of acne.

Technical Solution

The present disclosure provides a patch for the alleviation and prevention of acne, including a biodegradable metal represented by Chemical Formula 1 below and having an anti-acne effect.

$$Mg_aZn_bX_c \qquad \text{[Chemical Formula 1]}$$

In Chemical Formula 1, a, b and c are wt % of individual components, a+b+c=100 wt %, 0≤a≤100, 0≤b≤100, and 0≤c≤10, among which a or b is the greatest, and X is at least one selected from the group consisting of Ca, Fe, Mn, Si, Na, Zr, Ce, and P.

In such a patch for the alleviation and prevention of acne, the biodegradable metal may be provided in the form of a microneedle or a thin plate.

In the patch for the alleviation and prevention of acne according to a preferred embodiment of the present disclosure, the biodegradable metal may be represented by Chemical Formula 1, in which a, b and c are wt % of individual components, a+b+c=100 wt %, i) 90≤a≤100, 0≤b≤10, and 0≤c≤10 or ii) 0≤a≤10, 90≤b≤100, and 0≤c≤10, and X is at least one selected from the group consisting of Ca, Fe, Mn, Si, Na, Zr, Ce, and P.

In the patch for the alleviation and prevention of acne according to the most preferred embodiment, the biodegradable metal may be Mg having a purity of 95% or more and containing inevitable impurities.

In the patch for the alleviation and prevention of acne according to an embodiment of the present disclosure, the biodegradable metal may include two or more metal phases to form a galvanic circuit to thus accelerate a degradation rate. Such a biodegradable metal may include an $Mg_2Ca$ phase, an MgZn phase or a $Ca_2Mg_6Zn_3$ phase.

In the patch for the alleviation and prevention of acne according to an embodiment of the present disclosure, the biodegradable metal may be configured such that the surface of the metal is coated with a second metal of a different type in order to form a galvanic circuit. Here, the second metal may be at least one metal selected from the group consisting of sodium, magnesium, potassium, iron, nickel, zinc, gallium, selenium, strontium, zirconium, molybdenum, niobium, tantalum, titanium, silicon, silver, gold, manganese, and calcium.

Another embodiment of the present disclosure provides a method of using the patch for the alleviation and prevention of acne as described above, including attaching the patch to skin suffering from acne.

In the method according to a preferred embodiment, a moisturizing step or a skin-soothing step may be performed before attaching the patch to the skin suffering from acne.

Advantageous Effects

According to the present disclosure, a patch using a biodegradable metal has antibacterial activity against an acne pathogen when used alone, without the need to additionally load a drug, so it is useful for the alleviation and prevention of acne. Through the simple method in which the patch is manufactured in various forms and is applied to the skin, the patch of the present disclosure can be effective at preventing acne or alleviating the generated acne.

BRIEF DESCRIPTION OF DRAWINGS

FIG. 15 is a table showing the unique factor of each section shown in FIG. 14 and the global score in the acne severity assessment according to the global acne grading system (GAGS) in a clinical trial;

FIG. 16 is a table that categorizes the presence and severity of adverse reactions in the skin irritation evaluation in a clinical trial.

BEST MODE

Figure 1:
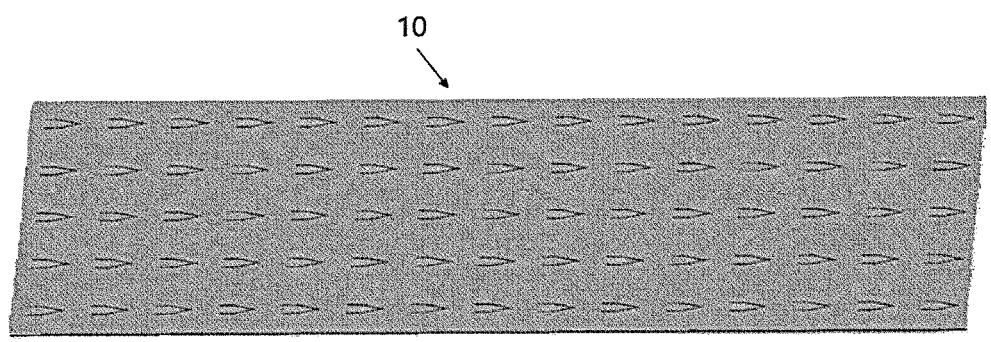
FIG. 1 is an exploded view of a microneedle obtained by subjecting a sheet made of a biodegradable metal to microneedle processing.

Acne is a chronic inflammatory disease of the pilosebaceous unit, and causes various skin changes such as comedones (hardened sebum in the hair follicles), papules (raised skin lesions less than 1 cm in size), pustules, nodules, pseudocysts, etc., and thus concave scars or enlarged scars may be left as sequelae thereof. Acne occurs concentratedly on the face, neck, chest and the like where sebaceous glands are gathered, and is a disease in which the sebaceous glands attached to the hair follicles that form hair are inflamed.

The exact cause of acne has not been identified, but acne is deemed to occur due to multiple causes in combination rather than a single cause. The major cause thereof is that, during puberty, secretion from the sebaceous glands is vigorous due to an excess of male hormones and the epithelium of the hair follicles causes dyskeratosis (abnormal keratinization showing incomplete and immature keratinization), and the hair follicles are blocked, forming comedones, which are the basic lesions of acne.

In acne development caused by bacteria, a known pathogen of acne is *Propionibacterium acnes*, among microorganisms residing in the hair follicles. This acne pathogen is the main cause of troubles while eating and growing sebum. In normal people, even though such bacteria are present on the skin, no problems occur, but in the case in which the hair follicles are blocked and sebum accumulates in the hair follicles, such bacteria eat sebum and grow rapidly.

Moreover, this acne pathogen excretes a fatty acid that is a substance similar to butter after eating fat (triglyceride). Such a chemical change causes the healthy, weakly acidic skin to become alkalized due to the pH imbalance of oil thereon, resulting in deterioration of the skin's own function and creating a vicious cycle that further harms the skin. In order to prevent and alleviate acne caused by *Propionibacterium acnes*, therapeutic methods using applicable drugs or edible drugs have been commonly proposed.

Meanwhile, a microneedle using a biodegradable metal was developed by the present applicant and filed (Korean Patent Application Publication No. 2017-0115449).

In the present disclosure, based on the results of thorough research into the microneedle thus developed, it has been confirmed that the corresponding biodegradable metal exhibits antibacterial activity against the acne pathogen *Propionibacterium acnes*, and thus novel use of the biodegradable metal is devised.

In the present disclosure, the description in connection with the biocompatible metal, the method of manufacturing the same in a microneedle form, and a series of metallic reactions occurring on the skin follows Korean Patent Application Publication No. 2017-0115449.

However, in the present disclosure, it is found that the biodegradable metal is not limited only to the use as a microneedle for a drug carrier, but acts alone as a functional configuration having antibacterial activity against the acne pathogen.

In the present disclosure, a biodegradable metal using magnesium or zinc alone or in a combination with a metal of a different type such as calcium, etc. is manufactured in the form of a thin plate or a microneedle, and the antibacterial activity thereof against an acne pathogen is evaluated. As a result, it is confirmed that the biodegradable metal manufactured using magnesium, calcium, or zinc alone or an alloy thereof with a metal of a different type in a specific amount has antibacterial activity when used alone, even without the need to additionally include a drug.

Accordingly, an aspect of the present disclosure pertains to a patch for the alleviation and prevention of acne including a biodegradable metal represented by Chemical Formula 1 below and having an anti-acne effect.

$$Mg_a Zn_b X_c \quad \text{[Chemical Formula 1]}$$

In Chemical Formula 1 a, b and c are wt % of individual components, a+b+c=100 wt %, 0≤a≤100, 0≤b≤100, and 0≤c≤10, among which a or b is the greatest, and X is at least one selected from the group consisting of Ca, Fe, Mn, Si, Na, Zr, Ce, and P.

It is preferred that the biodegradable metal contain mainly magnesium or zinc. Therefore, in Chemical Formula 1, a, b and c are wt % of individual components, a+b+c=100 wt %, i) 90≤a≤100, 0≤b≤10, and 0≤c≤10 or ii) 0≤a≤10, 90≤b≤100, and 0≤c≤10, and X is at least one selected from the group consisting of Ca, Fe, Mn, Si, Na, Zr, Ce, and P.

The biodegradable metal according to the present disclosure is a metal that is attached to or inserted into the subcutaneous or epithelial region and then absorbed and degraded to thus release metal ions and degradation products into the body. Magnesium (Mg), calcium (Ca), zinc (Zn), etc., which are alkaline-earth-metal-based biodegradable metals, have a mechanism for releasing hydrogen gas by reacting with water, as represented in Schemes 1 to 3 below.

$$Mg+2H_2O \rightarrow Mg(OH)_2+H_2 \text{ (gas)} \quad \text{[Scheme 1]}$$

$$Ca+2H_2O \rightarrow Ca(OH)_2+H_2 \text{ (gas)} \quad \text{[Scheme 2]}$$

$$Zn+2H_2O \rightarrow Zn(OH)_2+H_2 \text{ (gas)} \quad \text{[Scheme 3]}$$

In the present disclosure, it is preferred that the biodegradable metal be composed exclusively of magnesium (Mg), zinc (Zn), etc. In particular, in view of exhibiting superior biocompatibility and non-toxicity in normal cells or tissues, a biodegradable metal composed of magnesium alone is most preferable. Here, the magnesium alone or zinc alone refers to pure magnesium or zinc having a purity of 95% or more and containing inevitable impurities generated in the metal production process.

In addition, the biodegradable metal may be manufactured using two or more metals to accelerate the degradation rate thereof in the subcutaneous or epithelial region, that is, to form a galvanic circuit. In the present disclosure, the biodegradable metal may be configured such that the surface of the biodegradable metal represented by Chemical Formula 1 may be coated with a second metal of a different type in order to form a galvanic circuit. Here, examples of the second metal may include, but are not limited to, sodium, magnesium, potassium, iron, nickel, zinc, gallium, selenium, strontium, zirconium, molybdenum, niobium, tantalum, titanium, silicon, silver, gold, manganese, calcium, etc. In particular, chromium or nickel must not be included when iron (Fe) is included.

In the patch for the alleviation and prevention of acne according to the present disclosure, the biodegradable metal may be provided in the form of a thin plate or a microneedle. For example, the microneedle may be manufactured through a typical method of manufacturing a soluble microneedle in the industry, such as laser cutting, sheet metal processing, casting, etching, etc., and the manufacturing method thereof is not particularly limited. For example, as shown in FIG. 1, a thin-plate-type sheet 10 made of a biodegradable metal is manufactured, formed into a certain shape using a laser cutting machine (marking machine), and then bent using a jig press, thereby manufacturing a microneedle.

In the present disclosure, the patch containing such a biodegradable metal may be used alone for the purpose of alleviating and preventing acne, without the need to additionally apply or load a drug.

Figure 2:
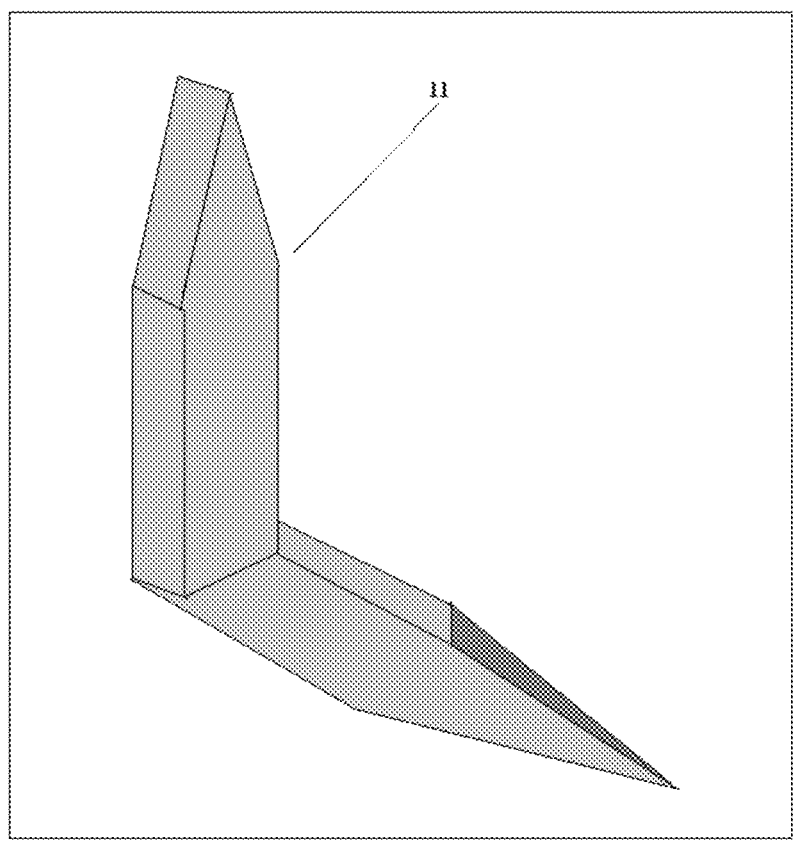
FIG. 2 schematically shows a microneedle obtained by subjecting the processed microneedle to bending.

FIG. 2 schematically shows a microneedle 11 obtained by subjecting the processed microneedle to bending in order to penetrate the skin.

Figure 3:
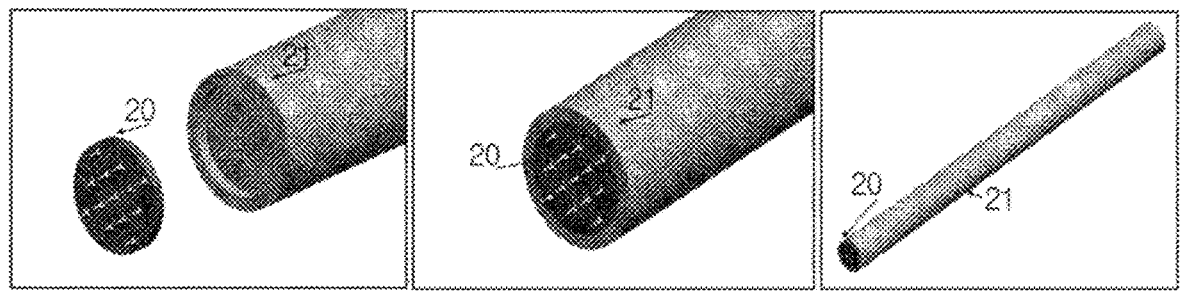
FIG. 3 schematically shows a tip-type microneedle and a microneedle holder.

The microneedle according to the present disclosure may be provided in an integrated form, or may be configured to include a microneedle 20 and a microneedle holder 21, as shown in FIG. 3. In the microneedle using the microneedle holder 21, needles may be deliberately left behind in the subcutaneous region by applying distortion after the needles are inserted.

Figure 4A:
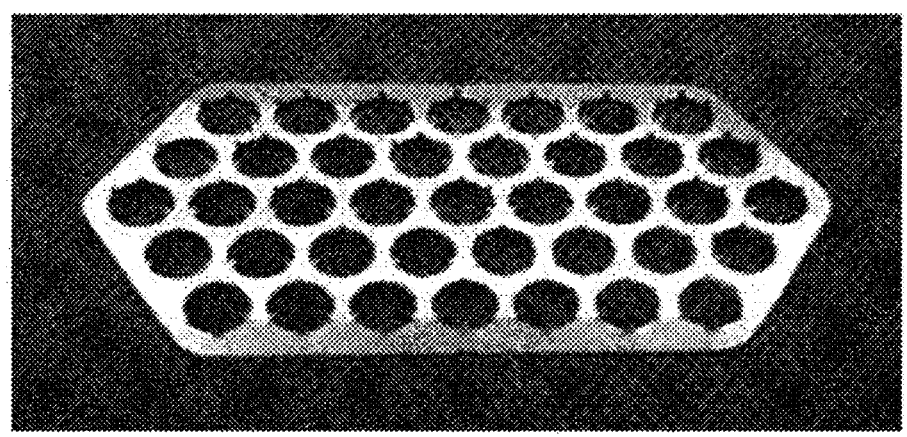
FIG. 4A is a photograph showing a microneedle prototype according to the present disclosure and FIG. 4B is a photograph showing the bendability thereof.
Figure 4B:
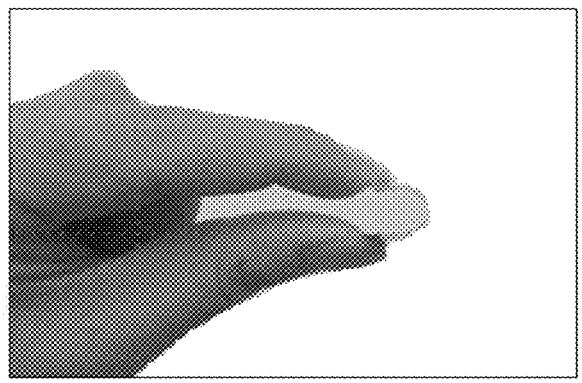

FIG. 4A is a photograph showing a microneedle prototype manufactured according to an embodiment of the present disclosure and FIG. 4B is a photograph showing the bendability thereof.

According to the present disclosure, in order to facilitate application of the microneedle to the skin, the microneedle may be manufactured in the form of a patch.

Figure 5A:
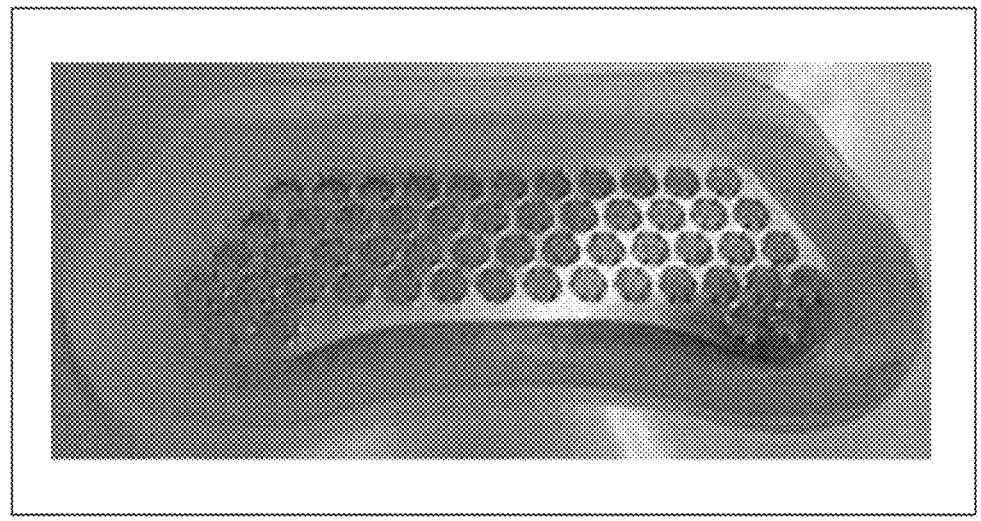
FIGS. 5A and 5B are photographs showing a microneedle patch according to the present disclosure (A: before use, B: after use)
Figure 5B:
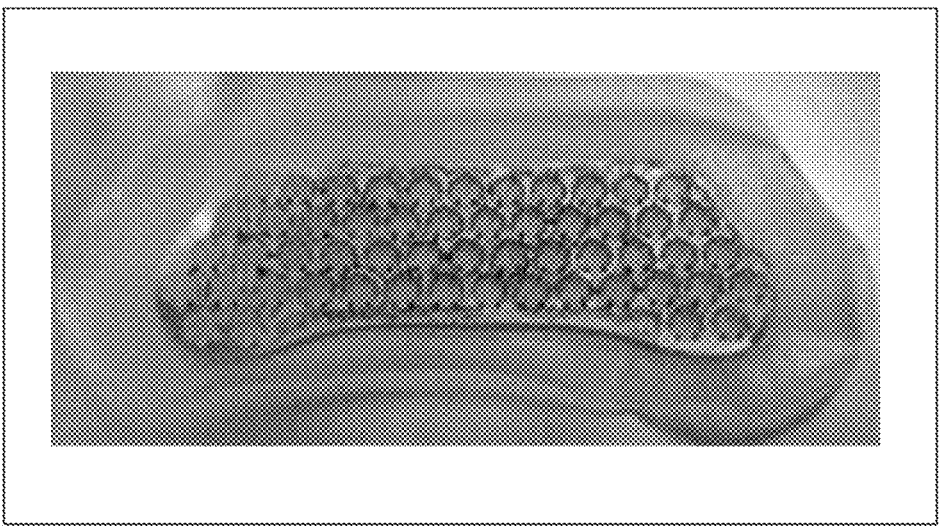

As shown in FIGS. 5A and 5B, the microneedle patch is used to fix the microneedle to the skin, and includes a microneedle and a patch unit formed on the surface of the microneedle opposite the surface on which needles are provided. There is no particular limitation on the size, shape, and material of the patch unit. As shown in FIG. 5B, the microneedle that is used may be discolored due to ionization in the subcutaneous region.

When the patch including the biodegradable metal according to the present disclosure is applied to the skin, it may exhibit an anti-acne effect when used alone, without the need to additionally include or apply a drug. In order to further increase the above effect or shorten the onset time of the effect, it is preferred that a moisturizing step or skin-soothing step be performed before attaching the patch of the present disclosure. Here, the moisturizing step may be performed through application of various moisturizing cosmetics, for example, toner or moisturizing mist, etc., and the skin-soothing step may be performed through application of functional cosmetics or medicines known to alleviate skin redness or acne, but the present disclosure is not limited thereto.

The moisturizing step or the skin-soothing step merely serves to assist the anti-acne effect of the patch including the biodegradable metal according to the present disclosure, and it is not required for this step to be first performed in order for the effect of the patch of the present disclosure to be realized.

The present disclosure aims to develop the novel use of the biodegradable metal in the form of a microneedle for the alleviation and prevention of acne. This use is intended to be confirmed through the following examples in a manner in which the activity of the biodegradable metal sample against various microorganisms present on the skin is evaluated and selective activity thereof against only the acne pathogen is exhibited.

MODE FOR DISCLOSURE

A better understanding of the present disclosure will be given through the following examples, and these examples are not to be construed as limiting the scope of the present disclosure.

Example 1

In order to evaluate the anti-acne activity of the biodegradable metal according to the present disclosure, samples were provided to the Korea Testing & Research Institute, and antibacterial and antifungal tests were performed in the following manner.

Figure 6:
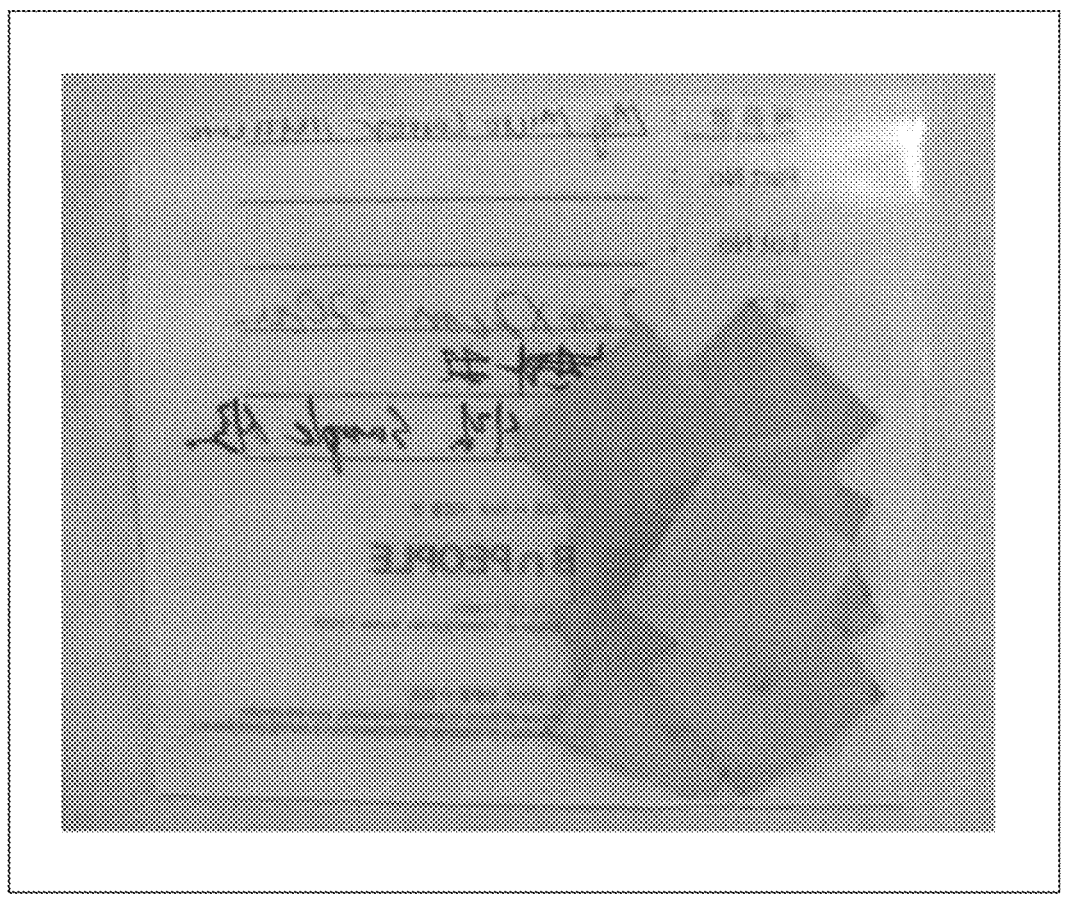
FIG. 6 is a photograph showing microneedle samples according to the present disclosure provided for an antimicrobial test.

The samples that were provided were sheets (having a thickness of 100 μm) manufactured using pure Mg (magnesium having a purity of 95% or more) containing inevitable impurities generated during the manufacture thereof, and were cut to a predetermined size and used as test samples, as shown in FIG. 6.

<Test Devices and Materials>
(1) Test Devices
Autoclave (Coretech, Korea)
Dry oven (Jisico, Korea)
Water bath (Polyscience, USA)
Incubator (Memmert, Germany)
pH meter (Thermo Orion, USA)
Stop watch (Time Art, Japan)
Vortex mixer (Thermolyne, USA)
Container (Iwaki Pyrex, Japan)
Sterile pipette (Falcon, USA)
Petri dish (SPL, Korea)
Volumetric flask (Myung Sung, Korea)
Mechanical shaker (Jisico, Korea)
Clean bench (Sugong Yanghaeng, Korea)
Colony counter (Deokwoo Science, Korea)
Anaerobic container (DIFCO, USA)
(2) Test Materials
1) Test Strain
Obtained from Korean Culture Center of Microorganisms
*Propionibacterium acnes* ATCC 6919
*Staphylococcus epidermidis* ATCC 12228
*Trichophyton rubrum* ATCC 28188
2) Medium and Reagent
Reinforced clostridial medium broth (DIFCO, USA)
Brain Heart Infusion broth (DIFCO, USA)
Sabouraud dextrose broth (DIFCO, USA)
Reinforced clostridial medium agar (DIFCO, USA)
Tryptic soy agar (DIFCO, USA)
Sabouraud dextrose agar (DIFCO, USA)
Gaspak™ EZ (DIFCO, USA)
0.05% polysorbate 80 solution
Sterile liquid paraffin
(3) Test Method
1) Test Method
a. Preculture of Test Pathogen and Preparation

*P. acnes* was inoculated into a reinforced clostridial medium (RCM) broth and cultured for 3 days at $(35\pm1)°$ C. The cultured pathogen solution was inoculated into a new RCM broth and cultured under the same conditions as above, and this procedure was repeated once more. Anaerobic conditions were maintained using sterile liquid paraffin throughout the process of culturing the strain. Thereafter, the resulting culture solution was used as a test pathogen solution.

*S. epidermidis* was inoculated into a Brain Heart Infusion broth, cultured at $(35\pm1)°$ C. for (18 to 24) hours, and then used as a test pathogen solution.

*T. rubrum* was inoculated into a Sabouraud dextrose agar and cultured at $(25\pm1)°$ C. for 14 days. A 0.05% polysorbate 80 solution was dispensed on a solid medium in which the test pathogen was grown, and the spores were separated using a spreader and then passed through gauze to remove the hyphae. The spore solution thus prepared was adjusted to $(1 \text{ to } 9)\times10^7$ CFU/mL and then used as a test pathogen solution.

b. Test Procedure

Each pathogen culture solution was evenly inoculated onto the previously prepared reinforced clostridial medium (RCM) agar, tryptic soy agar and Sabouraud dextrose agar using a sterile cotton swab, and the prepared sample (20 mm×20 mm) was placed on the center of the medium. Thereafter, *P. acnes* was cultured at $(35\pm1)°$ C. for 5 days under anaerobic conditions, *S. epidermidis* was cultured at $(35\pm1)°$ C. for $(24\pm2)$ hours, and *T. rubrum* was cultured at $(25\pm1)°$ C. for 7 days. Thereafter, the test was performed by measuring the zone of inhibition around the sample.

2) Results

The width W of the zone of inhibition was calculated using Equation 1 below.

$$W=(T-D)/2 \qquad \text{<Equation 1>}$$

W: width of zone of inhibition (mm)
T: total diameter of sample and zone of inhibition (mm)
D: diameter of sample (mm)

TABLE 1

| Test strain | T | D | W |
| --- | --- | --- | --- |
| P. acnes | 32 | 20 | 6.0 |
| S. epidermidis | 20 | 20 | 0.0 |
| T. rubrum | 20 | 20 | 0.0 |

Figure 7:
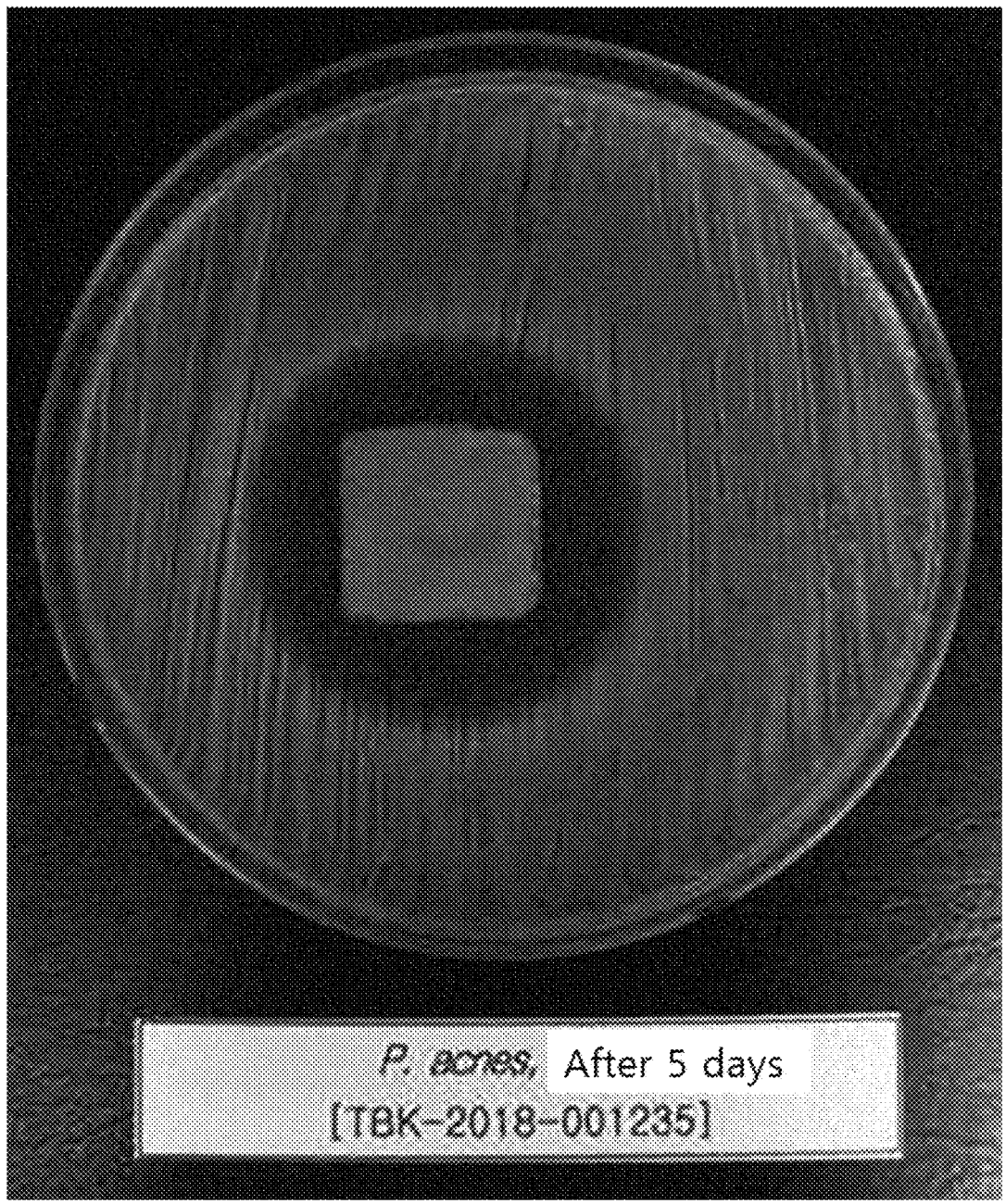
FIGS. 7 to 9 are photographs showing antibacterial or antifungal test results, FIG. 7 showing the results of a test on *Propionibacterium acnes* ATCC 6919, FIG. 8 showing the results of a test on *Staphylococcus epidermidis* ATCC 12228, and FIG. 9 showing the results of a test on *Trichophyton rubrum* ATCC 28188.

As summarized in Table 1 above, based on the results of the antibacterial effect on *P. acnes*, the total diameter T of the sample and the zone of inhibition was 32 mm, and the diameter D of the sample was observed to be 20 mm. Therefore, the width W of the zone of inhibition was determined to be 6.0 mm using the above calculation equation (FIG. 7).

Figure 8:
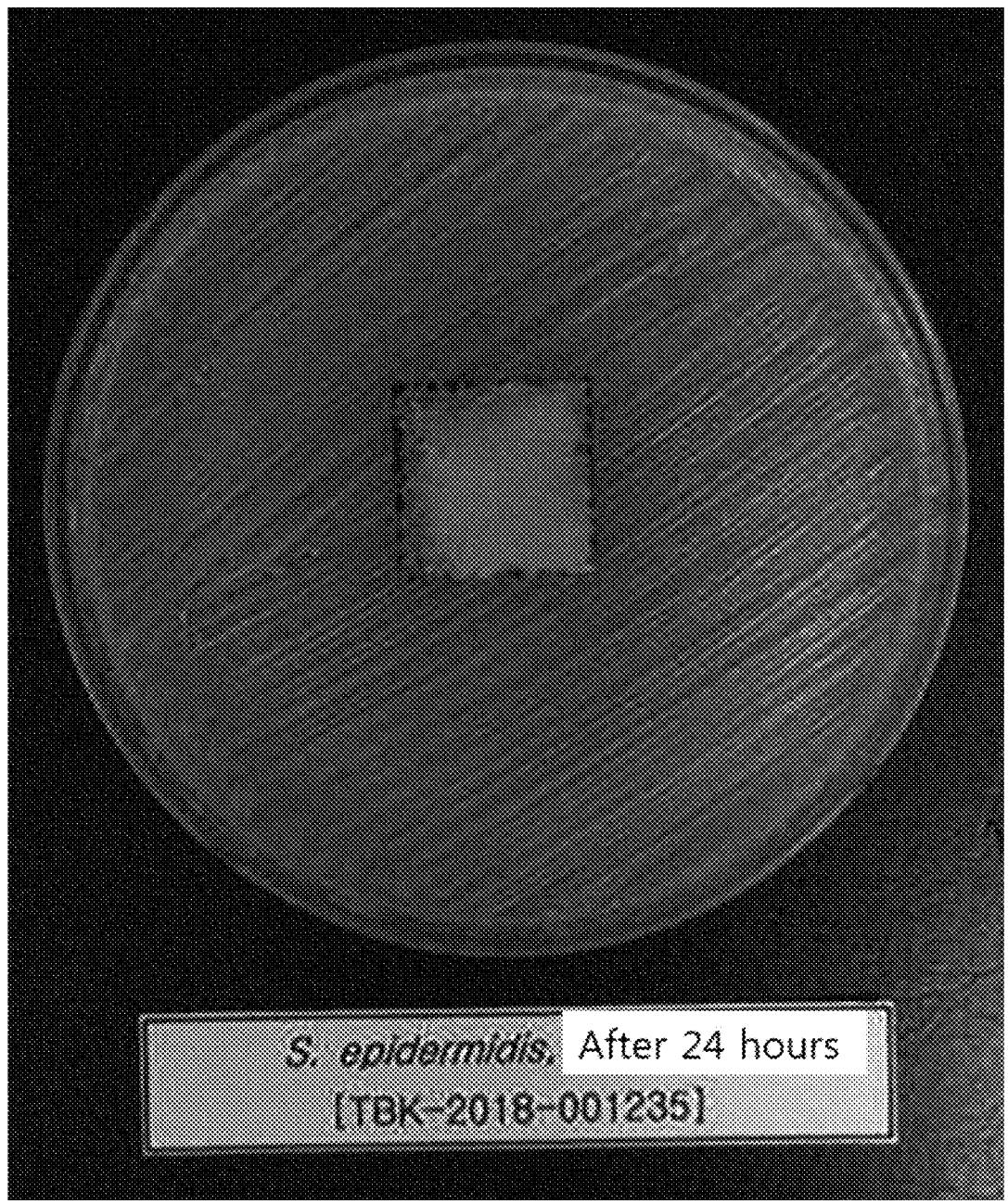

Based on the results of the antibacterial effect on *S. epidermidis*, the total diameter T of the sample and the zone of inhibition was 20 mm, and the diameter D of the sample was observed to be 20 mm. Therefore, the width W of the zone of inhibition was determined to be 0.0 mm using the above calculation equation (FIG. 8).

Figure 9:
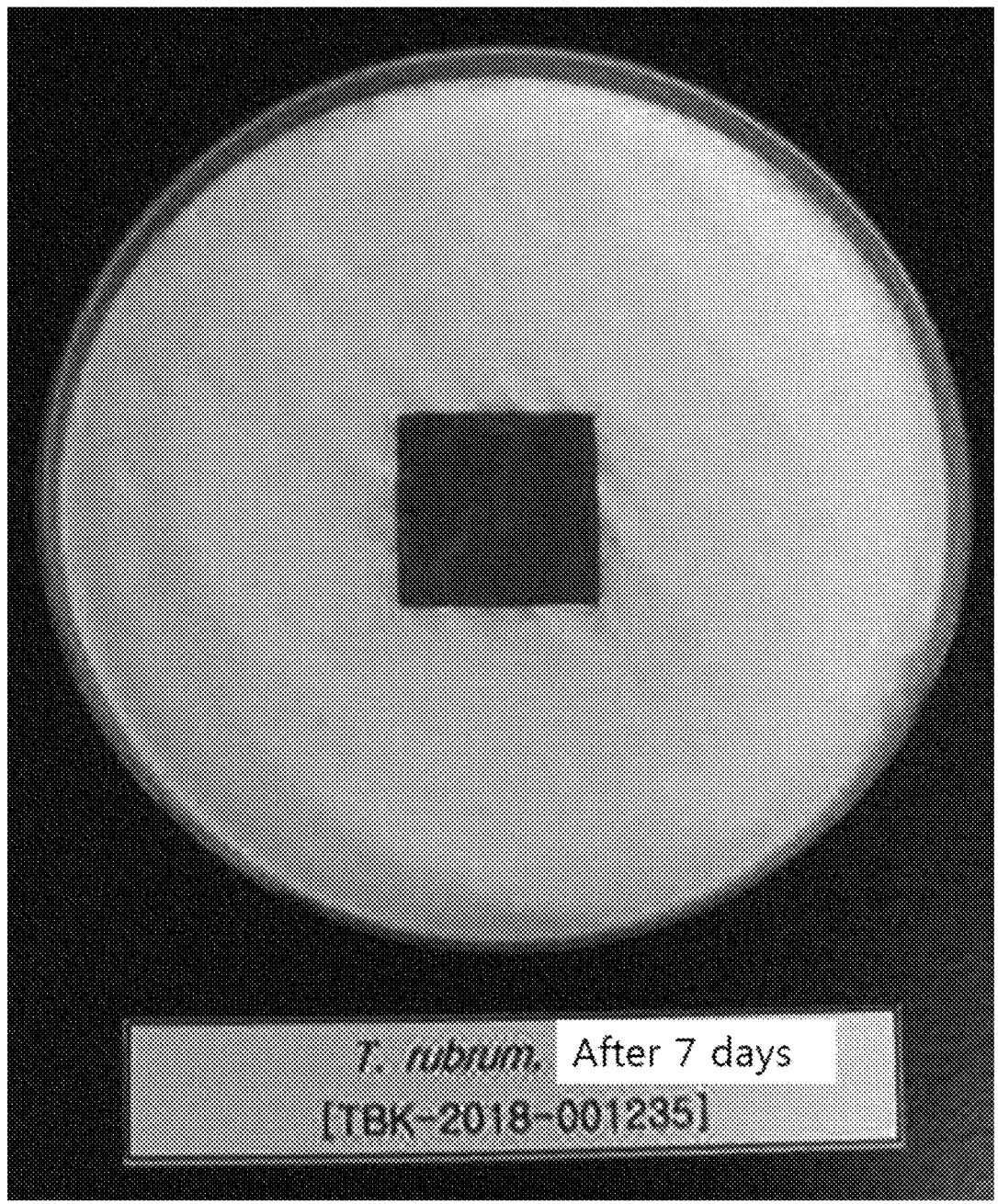

Based on the results of the antifungal effect on *T. rubrum*, the total diameter T of the sample and the zone of inhibition was 20 mm, and the diameter D of the sample was 20 mm. Therefore, the width W of the zone of inhibition was determined to be 0.0 mm using the above calculation equation (FIG. 9).

The widths of the zones of inhibition of *P. acnes*, *S. epidermidis* and *T. rubrum* by the sample [referred to as Mg Micro Carrier Multi Care] under the present test conditions were 6.0 mm, 0.0 mm and 0.0 mm, respectively.

Consequently, the biodegradable metal of the present disclosure had antibacterial activity against only the acne pathogen, and antibacterial or antifungal effects against the other pathogens were not observed.

<Example 2> Manufacture of Microneedle and Patch

The same biodegradable metal sheet as the sheet provided for the evaluation of the antibacterial activity of Example 1 was manufactured, after which a microneedle was manufactured using a laser marking machine (JTY FIBER MA20, JTW system). Here, the tip angles of the microneedle were 15°, 30° and 35°, and the needle heights were 0.5 mm, 1.0 mm and 1.5 mm.

A microneedle patch was manufactured by attaching a hydrocolloid patch coated with an adhesive to the surface of the microneedle opposite the surface on which needles were formed. The microneedle patch thus manufactured was packaged and sterilized.

Figure 10:
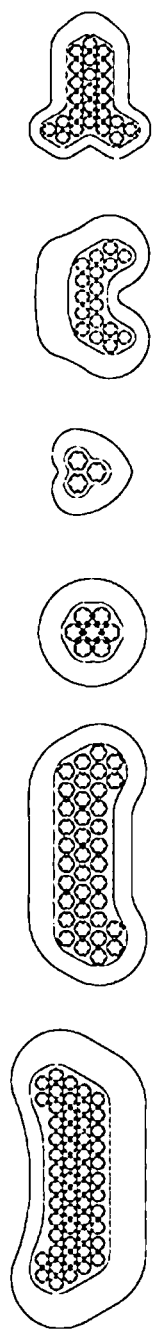
FIGS. 10 and 11 schematically show various shapes of the microneedle patch according to the present disclosure.
Figure 11:

Such a microneedle patch may be manufactured in various shapes for the alleviation and prevention of acne, and examples thereof are illustrated in FIGS. 10 and 11.

The microneedle patch thus obtained was attached after facial washing to any one of acne sites of seven 15-year-old boys with skin suffering from acne, and then the acne alleviation effect was observed for 7 days.

With regard to the evaluation criteria, the case in which the acne treatment effect is remarkable, that is, the case in which the area of skin suffering from acne is clearly reduced and the extent of acne inflammation is also clearly reduced, is awarded a score of 5, the case in which the extent of such alleviation is moderate is awarded a score of 4, the case in which the extent of such alleviation is mild is awarded a score of 3, the case in which there is no change is awarded a score of 2, and the case in which the acne is worsened is awarded a score of 1, after which comprehensive judgment was made based on the total score, and the results thereof are shown in Table 2 below.

TABLE 2

| | Subject 1 | Subject 2 | Subject 3 | Subject 4 | Subject 5 | Subject 6 | Subject 7 | Total score |
|---|---|---|---|---|---|---|---|---|
| Microneedle patch of the present disclosure | 5 | 5 | 5 | 4 | 4 | 5 | 4 | 32 |

As is apparent from Table 2, it can be found that the evaluation results of the majority of subjects corresponded to a score of 5, indicating that the microneedle patch of the present disclosure has a notable effect on the alleviation of acne.

Figure 12:
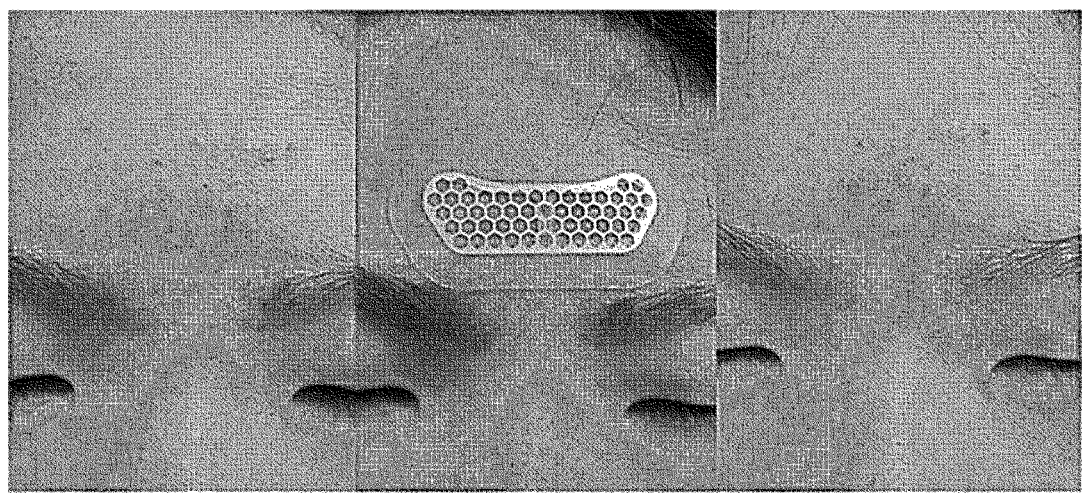
FIG. 12 is photographs showing the results of sensory evaluation using the microneedle patch according to the present disclosure, in detail, showing the skin condition before attachment (left), state of attachment (center), and the skin condition 8 hours after attachment (right)

Meanwhile, FIG. 12 shows the skin condition (left) before attachment of the microneedle patch to the subject having acne on the forehead, the state of attachment (center), and the skin condition (right) 8 hours after attachment, indicative of the immediate acne alleviation effect 8 hours after attachment of the microneedle patch of the present disclosure.

<Example 3> Clinical Trial

In order to evaluate whether the biodegradable metal of the present disclosure is suitable for use on skin suffering from acne, a clinical evaluation was performed in the following manner by the Chungcheongbuk-do Global Cosmeceutical Center.

(1) Test Method

A test was carried out on adult males and females aged 18 to 40 years. The test product was used once a day on the test site in accordance with the prescribed method of use, and the effect thereof was observed through visual evaluation. The evaluation was carried out in accordance with the Center's internal guidelines (SOP), and, with regard to matters not specified in the Ministry of Food and Drug Safety notification, reference was made to the References cited herein. The test site was the facial portion of the test subject.

The prescribed method of use was as follows.

① After thoroughly washing the face, tidy up the skin.

② Remove the cap of a syringe containing a high-concentration Centella ampoule (having a moisturizing or soothing effect).

③ Drop an appropriate amount of the high-concentration Centella ampoule on the microcarrier of a magnesium patch (made of magnesium having a purity of 95% or more).

④ Remove a protective film without touching the magnesium patch.

⑤ Before bedtime, closely attach the patch to the treatment location, and then press the patch several times so as to stimulate the skin.

⑥ The next morning, remove the patch.

⑦ Attach a hydrocolloid band to the location from which the patch was removed and keep it there throughout the day.

Figure 13:
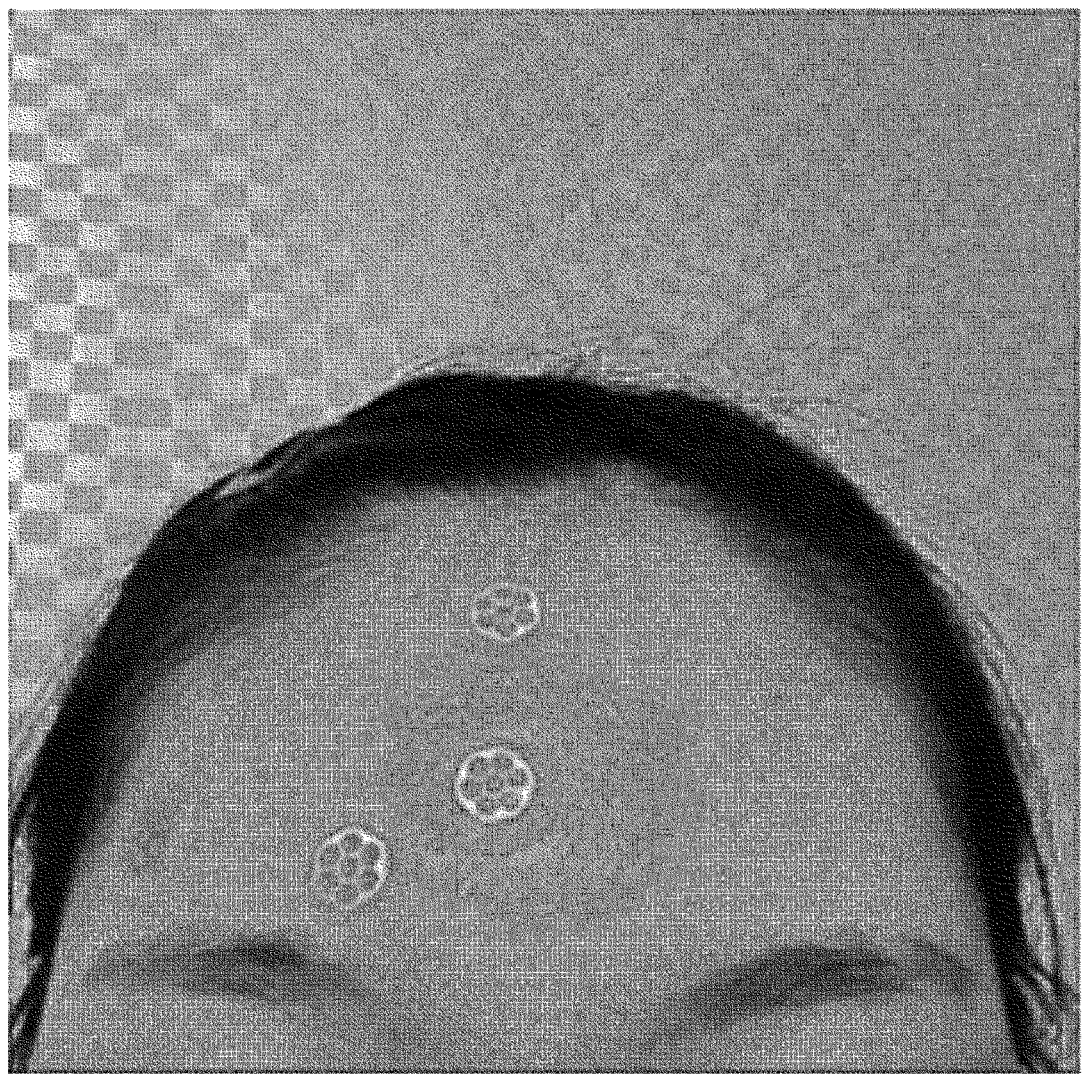
FIG. 13 is a photograph showing the microneedle patch according to the present disclosure attached to a test subject in a clinical trial.

An example of applying the magnesium patch to the test subject is shown in FIG. 13.

The test was performed by selecting 20 persons as test subjects who met the selection criteria and to whom the exclusion criteria did not apply.

After selecting test subjects suitable for the study in accordance with the selection and exclusion criteria, the skin condition of the test subjects was observed, and visual evaluation and photography (VISIA-CR) were performed before product use (0 day), 1 day after product use, 3 days after product use, 4 days after product use, and 5 days after product use.

(2) Measurement and Evaluation Method

1) Preparation Step

For the evaluation, the test subjects were stabilized for 30 minutes in a waiting room under constant-temperature and constant-humidity conditions (22±2° C., 40-60% RH) such that the skin surface temperature and humidity were adapted to the environment of the measurement space. For objective measurement, device evaluation was performed by one researcher at the same site every time measurement and visual evaluation was performed by two researchers.

2) Photographing

The entire face of each subject was photographed using a facial imaging system (VISIA-CR, Canfield, USA) equipped with a camera (Canon, EOS6D, JAPAN), and a Standard 2 measurement mode was used therefor. The facial imaging system (VISIA-CR, Canfield) was used in the state in which the forehead and chin of the test subject were fixed in order to minimize the subject's movement, and a gray card was used therewith to correct for changes in light levels upon photographing. Measurement was performed before product use (0 day), 1 day after product use, 3 days after product use, and 5 days after product use. The overlay function was used to photograph the same site, and only images were utilized in the present study.

3) Visual Evaluation

The visual evaluation was performed through a double-blind test by two experts.

When there was a difference in the evaluation between the two experts, the suitability was evaluated by selecting the lower level, and the adverse skin reaction was evaluated by selecting the higher level.

Figure 14:
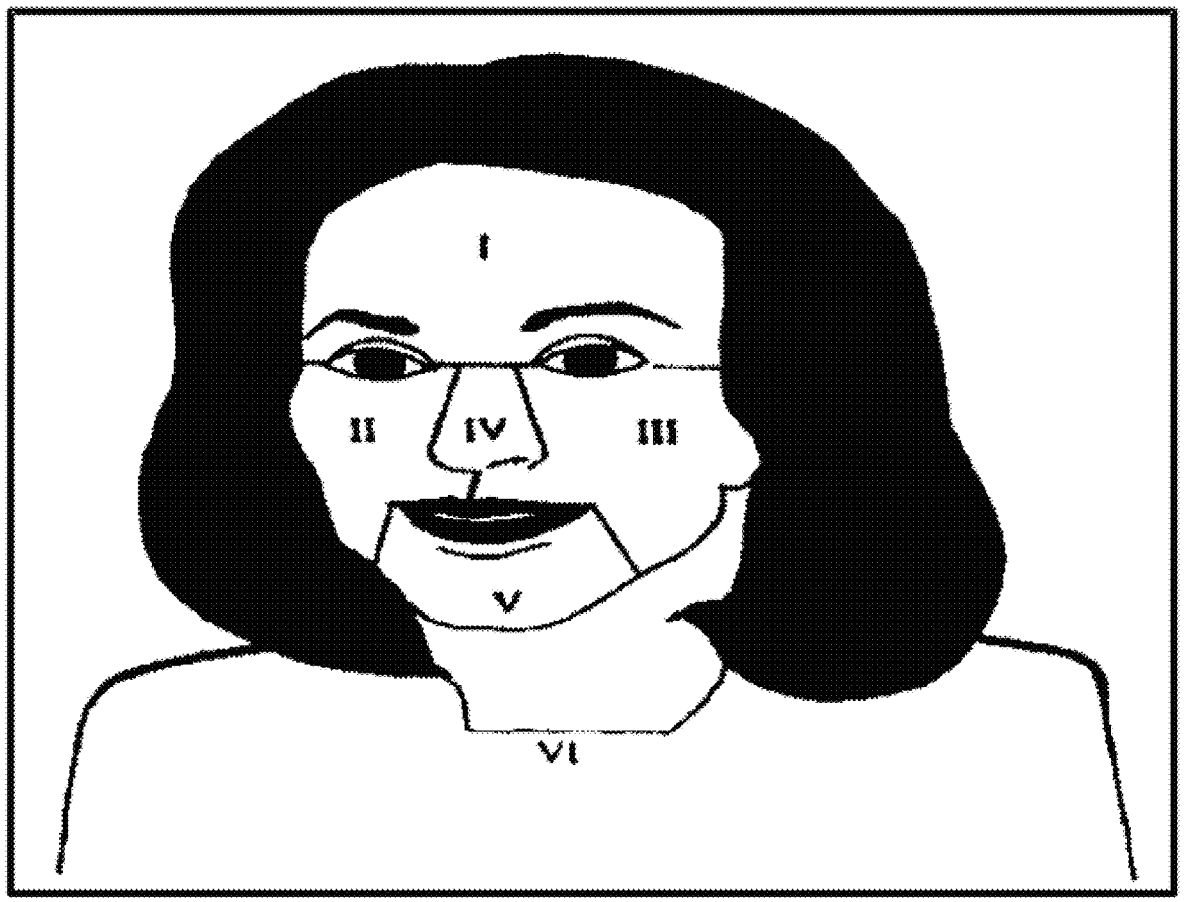
FIG. 14 is an image showing a test site in which the facial region is divided into 6 sections for acne severity assessment according to the global acne grading system (GAGS) in a clinical trial.

The visual evaluation was performed through the global acne grading system (GAGS). In GAGS, the face, chest, and back regions were divided into 6 sections depending on the surface-area distribution and density of the pilosebaceous units, a unique factor was assigned to each section, and a local score was assigned at the lesion site, and applied to the global score, followed by grading and evaluation. The six sections are as shown in FIG. 14.

Moreover, the unique factor of each section and the global score are as shown in FIG. 15.

4) Survey Evaluation

A survey was performed on the test product's general evaluation (sensation of use), change evaluation after use, satisfaction therewith, adverse reactions, etc. by each test subject upon the visit (5 days after product use).

a. Global Assessment of Efficacy

A survey was performed in a manner in which the test subjects directly answered a questionnaire on the measurement items after using the test product according to five levels: very satisfied (5), satisfied (4), neutral (3), dissatisfied (2), and very dissatisfied (1). The researcher determined the efficacy of the test product by representing, as a percentage, the number of test subjects providing each answer.

b. Survey Assessment of Product Preference

A survey was performed in a manner in which the test subjects directly answered a questionnaire on the test product and the sensation of use thereof. The evaluation items, particularly the general evaluation (sensation of use) and the satisfaction with the product, were evaluated according to five levels: very satisfied (5), satisfied (4), neutral (3), dissatisfied (2), and very dissatisfied (1).

5) Evaluation of Compliance

From the date of start of product use to the end thereof, whether or not the product was applied and whether or not an adverse reaction occurred were recorded in a daily compliance log.

6) Evaluation of Skin Irritation

Whether adverse reactions such as erythema, edema, scaling, itching, stinging, burning, tightness, prickling or other adverse reactions were caused by the test product was closely observed, and when the skin exhibited an adverse reaction, the grade was marked depending on the severity thereof and test opinions therefor were recorded. If the subject should become unable to participate in the test even when it is not the day of the subject visit, the subject was required to complete the "Agreement to renounce test participation" with signature attached.

The table that categorizes the presence and severity of adverse reactions is shown in FIG. 16.

(3) Analysis of Results

1) Visual Evaluation

The visual evaluation results were obtained by comparing the difference before and after product use, and the evaluation method was based on the method described in 3) of (2) above.

2) Statistical Analysis

Changes after product use were evaluated using a paired t-test and statistical results were regarded as statistically significant when the significant difference was 5% ($p<0.05$), which is the most frequently used in biological statistical analysis.

3) Survey Evaluation

The evaluation was based on the results of a survey assessment on efficacy and product preference.

4) The statistical analysis program that was used was SPSS version 10.0 software.

(4) Results

The test subjects who participated in the present human application test were 20 healthy adult males and females with an average age of 21.9±2.9 years, and all 20 subjects who participated in the test completed the final test without dropping out.

1) Results of Visual Evaluation

Based on the results of visual evaluation, it was confirmed that the evaluation grade through the global score decreased from moderate to mild in some test subjects, and the evaluation grade through the global score by all of the test subjects was mild, indicating that there was no significant change.

Meanwhile, the test product showed a statistically significant difference at each of 1 day after product use, 3 days after product use, and 5 days after product use compared to before product use (day 0) ($p<0.05$).

During the evaluation period, adverse effects on the skin due to the test product did not occur, and the analysis results thereof are shown in Table 3 below.

TABLE 3

| Measurement time | Before product use (day 0) | 1 day after product use | 3 days after product use | 5 days after product use |
|---|---|---|---|---|
| Grade | Mild | Mild | Mild | Mild |
| Visual evaluation (mean ± standard deviation, unit: Score) | 17.7 ± 3.3 | 16.3 ± 4.0 | 15.9 ± 3.6 | 15.4 ± 4.2 |
| p-value | — | 0.005 ($p<0.05$) | 0.012 ($p<0.05$) | 0.003 ($p<0.05$) |

2) Survey Results a. Survey Results for Assessment of Efficacy

The results of a survey conducted on the measurement items after use of the test product are shown in Table 4 below.

TABLE 4

| | Number of test subjects (percentage, %) | | | | | | Standard |
|---|---|---|---|---|---|---|---|
| | *5 | *4 | *3 | *2 | *1 | Mean | deviation |
| Acne alleviation effect | 6 (30.0) | 14 (70.0) | 0 (0.0) | 0 (0.0) | 0 (0.0) | 4.3 | 0.5 |

(Note) 5: very satisfied, 4: satisfied, 3: neutral, 2: dissatisfied, 1: very dissatisfied Based on the results of survey evaluation, the acne alleviation effect item was evaluated to be 'satisfied' or more by 100% of the test subjects.

b. Survey Results for Assessment of Preference

The preference felt by the test subjects for satisfaction with the product after product use, the sensation of use, and the change after use was surveyed. The results thereof are shown in Table 5 below.

TABLE 5

| | Number of test subjects (percentage, %) | | | | | | Standard |
|---|---|---|---|---|---|---|---|
| | *5 | *4 | *3 | *2 | *1 | Mean | deviation |
| Product color | 12 (60.0) | 7 (35.0) | 1 (5.0) | 0 (0.0) | 0 (0.0) | 4.6 | 0.6 |
| Product viscosity | 12 (60.0) | 7 (35.0) | 1 (5.0) | 0 (0.0) | 0 (0.0) | 4.6 | 0.6 |
| Extent of stimulation | 6 (30.0) | 9 (45.0) | 5 (25.0) | 0 (0.0) | 0 (0.0) | 4.1 | 0.8 |
| Extent of skin absorption | 6 (30.0) | 8 (40.0) | 5 (25.0) | 1 (5.0) | 0 (0.0) | 4.0 | 0.9 |
| Adhesion | 6 (30.0) | 7 (35.0) | 6 (30.0) | 1 (5.0) | 0 (0.0) | 3.9 | 0.9 |

TABLE 5-continued

|  | Number of test subjects (percentage, %) | | | | | Mean | Standard deviation |
|---|---|---|---|---|---|---|---|
|  | *5 | *4 | *3 | *2 | *1 |  |  |
| Softness | 5 (25.0) | 12 (60.0) | 3 (15.0) | 0 (0.0) | 0 (0.0) | 4.1 | 0.6 |
| Moisturizing effect | 7 (35.0) | 6 (30.0) | 7 (35.0) | 0 (0.0) | 0 (0.0) | 4.0 | 0.9 |
| Sebum reduction effect | 4 (20.0) | 14 (70.0) | 2 (10.0) | 0 (0.0) | 0 (0.0) | 4.1 | 0.6 |

(Note) 5: very satisfied, 4: satisfied, 3: neutral, 2: dissatisfied, 1: very dissatisfied Based on the results of survey evaluation, the color and viscosity items with regard to the satisfaction with the product were evaluated to be 'neutral' or more by 100% of the test subjects. With regard to the sensation of use, the extent of stimulation was evaluated to be 'neutral' or more by 100% of the test subjects, and the extent of skin absorption and adhesion were evaluated to be 'neutral' or more by 95% of the test subjects. In addition, with regard to the change after use, softness, moisturization, and sebum reduction effect were evaluated to be 'neutral' or more by 100% of the test subjects.

3) Evaluation of Skin Irritation

The results of evaluation of skin irritation (self-evaluation) on the test subjects are shown in Table 6 below.

TABLE 6

|  | Erythema | Edema | Scaling | Itching | Stinging | Burning | Tightness | Prickling |
|---|---|---|---|---|---|---|---|---|
| 1 day after use | No | No | No | No | No | No | No | No |
| 3 days after use | No | No | No | No | No | No | No | No |
| 5 days after use | No | No | No | No | No | No | No | No |

The test subjects were to report to the researcher immediately upon the occurrence of adverse reactions. Also, whether skin irritation occurred was marked on the questionnaire. During the present test, based on the results of questionnaire survey by the test subjects, no adverse reactions on the skin by the test product were observed in any of the test subjects.

Moreover, even in the visual evaluation by the researcher, adverse skin reactions were not observed.

4) Photographing Results

Figure 17:
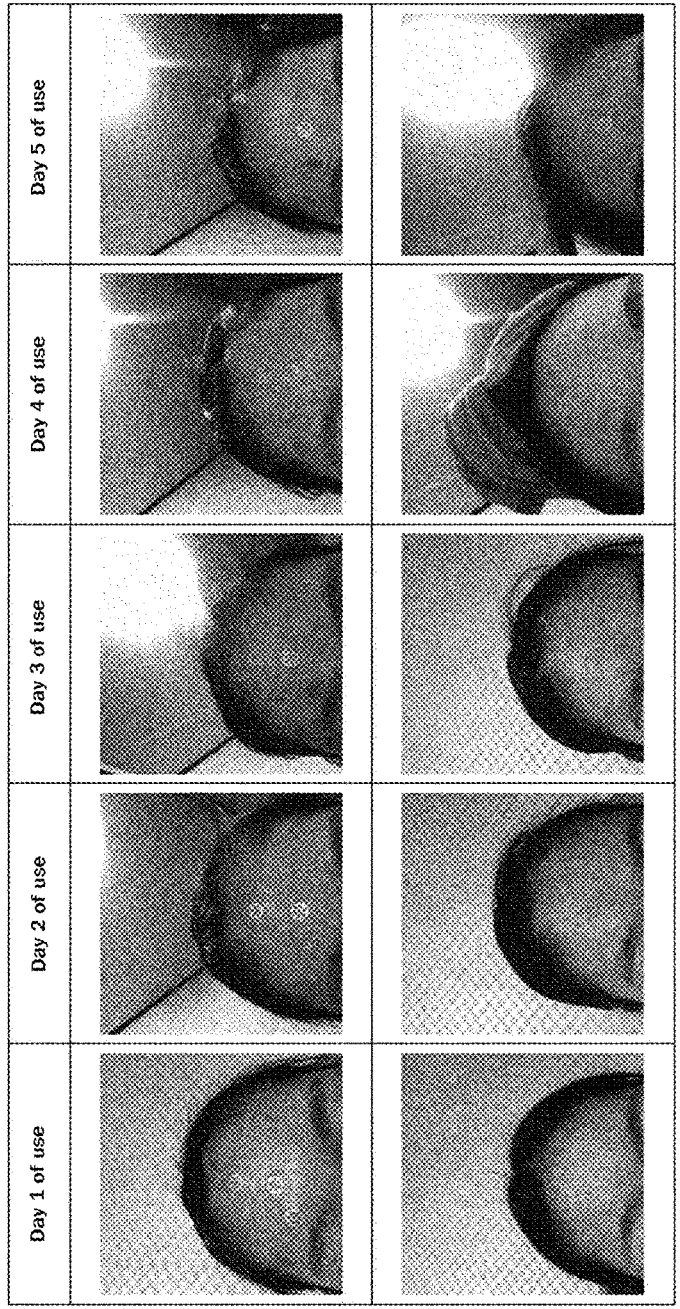
FIG. 17 is photographs taken throughout the test period after attachment of a magnesium microneedle patch to a test subject in a clinical trial.

All of the test subjects were photographed, and not all are shown herein, and only some are illustrated in FIG. 17.

As shown in FIG. 17, the shape of the magnesium patch used as the test material or the form of attachment thereof were confirmed, from which the basis of visual observation of the acne alleviation effect can be found.

The skin irritation evaluation and skin penetration effects of the microneedle and the microneedle patch for acne alleviation and prevention according to the present disclosure have been proven through the experiments of Korean Patent Application Publication No. 2017-0115449 filed and laid open by the present applicant. Thereby, the patch including the biodegradable metal of the present disclosure does not show toxicity in normal cells or tissues and can penetrate the skin without irritation to the skin, ultimately exhibiting antibacterial activity against the acne pathogen, which can contribute to simple and safe acne alleviation and prevention.

Also, the major cause of the selective anti-acne activity of the patch including the non-toxic biodegradable metal having high biocompatibility is assumed to be the locally increased pH due to the generation of $OH^-$ ions in the process of degradation of the metal, as represented in Schemes 1 to 3. When pure magnesium or pure zinc metal includes the components of Chemical Formula 1 to thus accelerate the degradation rate thereof, a more rapid antibacterial effect is expected.

INDUSTRIAL APPLICABILITY

The patch using the biodegradable metal of the present disclosure has antibacterial activity when used alone against an acne pathogen without the need to additionally load a drug, and is useful for the alleviation and prevention of acne. Through a simple method in which the patch is manufactured in various forms and is applied to the skin, the patch of the present disclosure can be useful for the prevention of acne or the alleviation of generated acne.

The invention claimed is:

1. A patch for alleviation and prevention of acne, comprising a biodegradable metal represented by Chemical Formula 1 below and having an anti-acne effect as the biodegradable metal degrades:

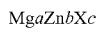

[Chemical Formula 1]

in Chemical Formula 1, a, b and c are wt % of individual components, a+b+c=100 wt %, 0≤a≤100, 0≤b≤100, and 0≤c≤10, among which a or b is greatest, and X is at least one selected from the group consisting of Ca, Fe, Mn, Si, Na, Zr, Ce, and P, wherein the biodegradable metal is provided in a form of a microneedle, and the microneedle is subject to bending when the patch is applied.

2. The patch of claim 1, wherein the biodegradable metal is provided in a form of a thin plate.

3. The patch of claim 1, wherein, in Chemical Formula 1, a, b and c are wt % of individual components, a+b+c=100 wt %, i) 90≤a≤100, 0≤b≤10, and 0≤c≤10 or ii) 0≤a≤10, 90≤b≤100, and 0≤c≤10, and X is at least one selected from the group consisting of Ca, Fe, Mn, Si, Na, Zr, Ce, and P.

4. The patch of claim 1, wherein the biodegradable metal is Mg having a purity of 95% or more and containing inevitable impurities.

5. The patch of claim 1, wherein the biodegradable metal comprises two or more metal phases to form a galvanic circuit to thus accelerate a degradation rate.

6. The patch of claim 5, wherein the biodegradable metal comprises an Mg2Ca phase.

7. The patch of claim 5, wherein the biodegradable metal comprises an MgZn phase.

8. The patch of claim 5, wherein the biodegradable metal comprises a Ca2Mg6Zn3 phase.

9. The patch of claim 1, wherein the biodegradable metal is configured such that a surface of the metal is coated with a second metal of a different type.

10. The patch of claim 9, wherein the second metal is at least one metal selected from the group consisting of sodium, magnesium, potassium, iron, nickel, zinc, gallium, selenium, strontium, zirconium, molybdenum, niobium, tantalum, titanium, silicon, silver, gold, manganese, and calcium.

11. A method of treating acne using the patch of claim 1, comprising attaching the patch to skin suffering from acne.

12. The method of treating acne using the patch according to claim 11, comprising performing a moisturizing step or a skin-soothing step before the attaching of the patch to the skin suffering from acne.

\* \* \* \* \*